US008573198B2

(12) United States Patent
Riggs et al.

(10) Patent No.: US 8,573,198 B2
(45) Date of Patent: Nov. 5, 2013

(54) DEVICES AND METHODS FOR AEROSOL THERAPY USING HYPERBARIC TONOMETRY

(75) Inventors: Johnny Harold Riggs, Mocksville, NC (US); Daniel J. Grady, Weaverville, NC (US)

(73) Assignee: Outcome Solutions, LLC, Greensboro, NC (US)

( * ) Notice: Subject to any disclaimer, the term of this patent is extended or adjusted under 35 U.S.C. 154(b) by 0 days.

(21) Appl. No.: 13/410,181

(22) Filed: Mar. 1, 2012

(65) Prior Publication Data

US 2013/0231591 A1 Sep. 5, 2013

(51) Int. Cl.
*A61M 15/00* (2006.01)
*A62B 7/02* (2006.01)
*A61K 9/12* (2006.01)

(52) U.S. Cl.
USPC ............ 128/202.17; 128/200.11; 128/201.21; 128/202.13; 128/202.16; 128/204.15; 424/45; 424/400; 424/489; 424/490

(58) Field of Classification Search
USPC ............ 128/200.11, 201.21, 202.13, 202.16, 128/202.17, 204.15; 424/45, 400, 489, 490
See application file for complete search history.

(56) References Cited

U.S. PATENT DOCUMENTS

| | | | |
|---|---|---|---|
| 4,919,895 A | 4/1990 | Heldebrandt et al. | |
| 5,084,011 A | 1/1992 | Grady | |
| 5,277,175 A | 1/1994 | Riggs et al. | |
| 6,537,246 B1 | 3/2003 | Unger et al. | |
| 6,649,145 B2 * | 11/2003 | McGrath et al. | 424/45 |
| 2007/0286809 A1 | 12/2007 | Williams et al. | |
| 2010/0121273 A1 | 5/2010 | Kochanek et al. | |
| 2011/0081384 A1 | 4/2011 | Archambeau et al. | |

FOREIGN PATENT DOCUMENTS

| | | |
|---|---|---|
| WO | 0004943 | 2/2000 |
| WO | 2010062628 A1 | 6/2010 |

OTHER PUBLICATIONS

Grady, Daniel J., et al. "Measurement of In Vitro Changes in Arterial Blood Gases Following Infusion of Supersaturated Dissolved Oxygen Solutions." Abstract. Respiratory Care, Oct. 2011. AARC, Irving, TX.
Grady, Daniel J., et al. "Measurement of Dissolved Oxygen Tension in Fluid Following Supersaturation of Fluid with Oxygen Gas Using a Novel Hyperbaric Tonometer." Abstract. Oct. 2011.
Ostrovksy, Gene. "Low-frequency Ultrasound for Chronic Wounds." 5 pages. Posting on MedGadget website. Dec. 4, 2007. http://medgadget.com/2007/12/lowfrequency_ultrasound_for_chronic_wounds.html.

(Continued)

*Primary Examiner* — Clinton T Ostrup
(74) *Attorney, Agent, or Firm* — Coats & Bennett, P.L.L.C.

(57) ABSTRACT

Methods and devices for creating a supersaturated liquid solution having dissolved gas with hyperbaric partial pressures and aerosolizing the supersaturated solution via a nebulizer. High partial pressures of the dissolved gas may be maintained before, during, and after the aerosolization process. Thus, the hyperbaric partial pressures may be retained in the aerosol particles even after the particles are exposed to ambient barometric pressure. The aerosolized particles may be inhaled to improve oxygenation and blood flow to the lung or alternatively, the aerosolized particles can be topically applied to accelerate wound healing. Nebulizers may produce aerosol particles in some embodiments have mass median aerodynamic diameters of between about 0.25 and about 5 microns, thereby allowing sufficient deposition in the lung parenchyma, proximal to alveoli. Supersaturated dissolved oxygen aerosol particles having mass median aerodynamic diameters greater than 10 microns may be used to accelerate wound healing when combined with ultrasound.

22 Claims, 15 Drawing Sheets

(56) References Cited

OTHER PUBLICATIONS

"What is Therapeutic Ultrasound?" Author unknown. 2 pages. Medical Products Online website. http://medicalproductsonline.org/whisthul.html.

"Therapeutic Ultrasound." Author unknown. 1 page. Online entry in Wikipedia, the free encyclopedia. http://en.wikipedia.org/wiki/Therapeutic_ultrasound.

Kochanek, Patrick. "The brain, the heart, and therapeutic hypothermia." Cleveland Clinic Journal of Medicine, vol. 76 • Suppl. 2. Apr. 2009. pp. S8-S12.

Jacobshagen, Claudius, et al., "Effects of large volume, ice-cold intravenous fluid infusion on respiratory function in cardiac arrest survivors" Resuscitation 80 (2009) 1223-1228. Elsevier.

Becker, Lance. "Cooling Heads and Hearts Versus Cooling Our Heels." Circulation 2010, 122:679-681. Aug. 2010. American Heart Association, Dallas, TX.

Bernard, Stephen, et al. "Induction of Therapeutic Hypothermia by Paramedics After Resuscitation From Out-of-Hospital Ventricular Fibrillation Cardiac Arrest : A Randomized Controlled Trial" Circulation 2010, 122:737-742. Aug. 2010. American Heart Association, Dallas, TX.

Lanphier, E.H. "Hydrogen Peroxide Infusion vs. Hyperbaric Oxygenation: Theoretical Considerations (Mar. 23, 1963)." Journal of Hyperbaric Medicine, vol. 7, No. 1, 1992. 8 pages. Undersea and Hyperbaric Medical Society. Durham, NC.

Durbin, Jr., Charles G. "Intravenous Oxygenation and CO2 Removal Device: IVOX." Respiratory Care, vol. 37, No. 2. Feb. 1992. pp. 147-153. AARC, Irving, TX.

Spears, Richard, et al., "Aqueous Oxygen: A Highly O2-Supersaturated Infusate for Regional Correction of Hypoxemia and Production of Hyperoxemia." Circulation, vol. 96, No. 12. Dec. 16, 1997. pp. 4385-4391.

Kim, Won Oak., et al., "Intravenous Oxygenation with Lactated Ringer's Solution." Journal of Korean Medical Science, vol. 2, No. 2, pp. 111-115. Jun. 1987.

Zhao, H., et al., "Investigations on Physiological Basis and Clinical Applications of Hyperoxia Solution for Treatment of Hypoxia." SAARC Journal of Anaesthesia, 2008: 1(2): 149-155.

"Protein shelled microbubbles for intravenous oxygen delivery." Author undeclared. Posting on Flintbox website, Nov. 17, 2011. 2 pages. Wellspring Worldwide, LLC. http://www.flintbox.com/public/project/8914/.

Sanders, Jack., et al., "Intravenous Oxygen and Pulmonary Embolism" Annals of Surgery, Aug. 1947. pp. 208-214. Wolters Kluwer/Lippincott, Williams & Wilkins.

Bourne, Geoffrey, et al., "The Value of Intravenous and Intraperitoneal Administration of Oxygen." Am J. Physiology, vol. 82, pp. 328-334. 1927.

Reissmann, Kurt, et al., "Is Intravenous Oxygen Therapy Possible?" Current Researches in Anesthesia and Analgesia, Nov./Dec. 1953. pp. 426-430. International Anesthesia Research Society, San Francisco, CA.

"Things to Watch: IV Oxygenation: turning blue blood to red" Author unlisted. Posting on VectorOnline website, Children's Hospital, Boston. 1 page. http://www.childrenshospital.org/.

Borden, Mark, et al., "Microbubbles for Intravenous Oxygenation." Online posting. 1 page. http://aiche.confex.com/aiche/2008/techprogram/P132164.HTM. American Institute of Chemical Engineers.

"Hillman and Borden win CAREER Awards." Author unlisted. Online posting, Columbia University Engineering Dept. Description of Borden's project on microscale bubbles technology for intravenous oxygenation. 1 page. http://www.engineering.columbia.edu/hillman-and-borden-win-career-awards.

List of Articles and Abstracts on Aqueous Oxygen Therapy. 2 pages. TherOx, Inc. 1999.

Final Office Action mailed May 2, 2013. U.S. Appl. No. 13/410,164.

* cited by examiner

LEGEND
16: VALVE
20: GAS BLENDER
24: FLOWMETER
28: IV BAG
30: CONNECTOR
34: VALVE
37: VALVE
40: CONTACT DEVICE
46: REFRIGERATION UNIT
48: VALVE
50: HEAD
53: TUBING
58: TUBING
60: CONTAINER

LEGEND
40: CONTACT DEVICE
46: REFRIGERATION UNIT
50: HEAD
60: CONTAINER
113: STIRRING DEVICE
115: TUBE

LEGEND
200: CONTACT DEVICE
201: FLOWMETER
203: HEAD
204: OUTLET
205: COIL
206: TUBING
207: PUMP
208: COVER
209: COVER
210: CHAMBER

LEGEND
84: CONNECTOR
86: LIQUID PORT
60: CONTAINER
94: FILTER
100: TUBING
102: CONNECTOR

FIGURE 16

| Parameter | Pre Aerosolization | Post Aerosolization |
|---|---|---|
| Temperature (°C) | 37.0 | 28.0 |
| Ambient Barometric Pressure (mm Hg) | 703.5 | 705.7 |
| pH | 7.467 | 7.332 |
| $pO_2$ (mm Hg) | 625.1 | 720.8 |

DEVICES AND METHODS FOR AEROSOL THERAPY USING HYPERBARIC TONOMETRY

BACKGROUND

Multiple cardiopulmonary diseases result in tissue hypoxia, which is a deficiency of molecular oxygen available for cellular metabolism. Tissue hypoxia may have many causes, and treatment of hypoxia is conventionally directed to the cause of the hypoxia.

When hypoxia is caused by deficiencies in the partial pressure of oxygen in inspired gas diffusing across the alveolar capillary membrane in the lung, the treatment involves increasing the partial pressure of inspired oxygen in the inspired atmosphere. Conditions such as asthma, pneumonia, and adult respiratory distress syndrome are examples of diseases which may produce tissue hypoxia because of complex pathology within the lung.

Treatment of tissue hypoxia associated with these diseases may be accomplished via multiple devices such as masks, nasal cannula, endotracheal tubes, tracheostomy tubes, mechanical ventilators and various other devices that administer oxygen. However, because of lung pathologic states such as mucosal edema, atelectasis, and bronchoconstriction, gaseous oxygen inhalation with the aforementioned devices may insufficiently treat tissue hypoxia. In addition, the inhalation of gaseous oxygen may result in oxygen toxicity and barotrauma, when excessive concentrations and gas partial pressure is used during treatment.

Tissue hypoxia may occur when blood flow to the lung is altered or decreased, thereby mismatching ventilated lung units with perfused lung units. Conditions such as primary pulmonary hypertension, and adult respiratory distress syndrome are examples of conditions which may decrease blood flow due to pulmonary artery vasoconstriction. Medications which may be administered to treat these types of lung problems may include inhalation of gaseous nitric oxide which is intended to dilate the vasculature, decrease pulmonary vascular resistance, and improve lung blood flow. Ideally, the inhalation of gaseous nitric oxide would improve the matching of ventilation with perfusion in the lung and result in improved gas exchange. However, the inhalation of nitric oxide may be associated with several complications including methemoglobinemia, rebound vasoconstriction during weaning of the gas, and hypotension. In addition, nitric oxide is an extremely expensive treatment, and may require extended periods of gas inhalation at considerable cost.

SUMMARY

The present application is directed to creating a supersaturated liquid solution having dissolved gas with hyperbaric partial pressures and aerosolizing the supersaturated solution via a specially designed nebulizer.

The application includes methods for creating a supersaturated liquid which may be aerosolized and delivered to a patient for therapeutic purposes. The supersaturated liquid may be formed in a separate device and then delivered to a device that produces the aerosol and delivers it to the patient. The supersaturated liquid may also be formed in the device itself, after which the liquid is transformed into an aerosol and delivered to the patient.

The application discloses multiple types of devices which may create, aerosolize, and deliver the supersaturated liquid to patients. The devices may include: a nebulizer which may create supersaturation of the liquid of the aerosol within the nebulizer itself, with subsequent aerosolization and delivery to the patient; a nebulizer which may receive a supersaturated fluid from an external gas liquid device with subsequent aerosolization; a large volume nebulizer which may create the supersaturated liquid within the nebulizer, aerosolize the liquid, and deliver the aerosol to a patient continuously (as opposed to intermittent, short duration (e.g., 15 minute) treatments); a metered dose inhaler which contain supersaturated liquids for aerosol administration; and a nebulizer that creates mixtures of supersaturated gas for aerosol administration to a patient.

The aerosol particles may be delivered to the patient for inhalation and for topical treatments.

One embodiment is directed to a method of aerosol therapy. The method includes forming a non-blood liquid supersaturated with oxygen gas, with the liquid being at a temperature below at least 55° F. and at ambient pressure. The method further includes transforming the liquid into aerosol particles that remain supersaturated with the oxygen gas, with the aerosol particles remaining at a temperature below at least 55° F. The method also includes delivering the aerosol particles to the patient while the aerosol particles remain supersaturated with the oxygen gas.

The method may further include supersaturating the liquid with the oxygen gas and transforming the liquid into the aerosol particles in a common chamber. The method may include continuously delivering the supersaturated liquid into the chamber while transforming the liquid into the aerosol particles. The supersaturated liquid may be formed in a first chamber and transferred to a second chamber, and the aerosol particles are formed in the second chamber. The method may include transforming the liquid into the aerosol particles that include mass median aerodynamic diameters greater than about 10 microns for topical application. The method may also include applying ultrasound waves to the patient in combination with the aerosol particles.

Another embodiment is directed to a method of aerosol therapy. The method includes mixing a gas with a non-blood liquid while the liquid is at a decreased temperature of less than about 55° F. and at ambient pressure. The method includes maintaining the liquid in contact with the gas at ambient pressure and at less than about 55° F. until the partial pressure of the gas in the liquid reaches at least 760 mm Hg. The method includes transforming the liquid into aerosol particles with the partial pressure of the gas in the aerosol particles remaining at least 760 mm Hg. The method also includes delivering the aerosol particles to the patient.

In the method, the liquid may be at a temperature of less than about 55° F. during the mixing with the gas and while being transformed into the aerosol particles. The method may also include decreasing the temperature of the liquid to less than about 55° F. after the gas is in contact with the liquid. The method may include mixing the gas with the liquid until the partial pressure of the gas in the liquid reaches at least 760 mm Hg. in a first device, transferring the liquid to a second device, and transforming the liquid into the aerosol particles in the second device. The method may include continuously transferring the liquid to the second device while transforming the liquid into the aerosol particles. The method may include dripping the liquid into the second device. The method may include moving a refrigerant through a coil in the first device and cooling the liquid. The method may include transforming the liquid into the aerosol particles that include mass median aerodynamic diameters of between about 0.25 microns and about 5.0 microns for deposition in the lung parenchyma proximal to alveoli when the aerosol particles are delivered to the patient. The method may include transforming the liquid into the aerosol particles that include mass median aerodynamic diameters greater than about 10 microns for topical application and applying ultrasound waves to the patient in combination with the aerosol particles.

Another embodiment is directed to a method for aerosol therapy. The method includes containing a non-blood liquid at ambient pressure in a gas-liquid contact device in a nebulizer. The method includes introducing a gas into the gas-liquid contact device and bubbling the gas through the liquid, with the liquid being at a temperature of less than about 70° F. The method includes maintaining the liquid in contact with the gas at the ambient pressure and the liquid at less than about 70° F. until a partial pressure of the gas in the liquid is at least 760 mm Hg. The method includes transforming the liquid into aerosol particles within the gas-liquid contact device while maintaining the aerosol particles at less than about 70° F. and the partial pressure of the gas of at least 760 mm Hg. The method includes delivering the aerosol particles through an outlet in the gas-liquid contact device to the patient.

The method may also include moving a refrigerant into a reservoir on an exterior of the gas-liquid contact device and cooling the liquid and the aerosol particles in the gas-liquid contact device. The method may include moving a refrigerant through a coil in the gas-liquid contact device and cooling the liquid while the gas is bubbling through the liquid. The method may include moving a refrigerant through a coil in the gas-liquid contact device and cooling the aerosol particles. The method may include introducing a second gas into the gas-liquid contact device to form the aerosol particles and to move the aerosol particles through the outlet and to the patient. The method may include transforming the liquid into the aerosol particles that include mass median aerodynamic diameters of between about 0.25 microns and about 5.0 microns for deposition in the lung parenchyma proximal to alveoli when the aerosol particles are delivered to the patient. The method may include transforming the liquid into the aerosol particles that include mass median aerodynamic diameters greater than about 10 microns for topical application to the patient.

Another embodiment is directed to a nebulizer for aerosol therapy. The nebulizer includes a gas-liquid contact device; a first inlet in the gas-liquid contact device to receive a non-blood liquid; a second inlet in the gas-liquid contact device to receive a gas, with the second inlet being spaced away from the first inlet; a refrigeration unit operatively connected to the gas-liquid contact device to cool a liquid and aerosol particles in the gas-liquid contact device to less than about 55° F.; and an outlet in the gas-liquid contact device to output the aerosol particles.

The nebulizer may include the refrigeration unit with a reservoir that extends around at least a portion of an exterior of the gas-liquid contact device and is configured to contain a refrigerant to cool the gas-liquid contact device. The refrigeration unit may include a port to receive the refrigerant. The refrigeration unit may include a coil within an interior of the gas-liquid contact device to contain a refrigerant. The nebulizer may include a cooling chamber that contains the refrigerant and is isolated from the interior of the gas-liquid contact device to prevent communication between the refrigerant and the liquid and the aerosol particles, with the cooling chamber including an input that connects to a first section of the coil and an outlet that connects to a second section of the coil. The nebulizer may also include a pump within the cooling chamber to pump the refrigerant through the input, the coil, and the output.

The various aspects of the various embodiments may be used alone or in any combination, as is desired.

BRIEF DESCRIPTION OF THE DRAWINGS

FIG. 16 is a chart illustrating the increased partial pressure of oxygen in the aerosol produced using the invention.

DETAILED DESCRIPTION

The present application is directed to creating a supersaturated liquid solution having dissolved gas with hyperbaric partial pressures and aerosolizing the supersaturated solution via a aerosolizing device, such as a nebulizer. High partial pressures of the dissolved gas are maintained before, during, and after the aerosolization process. Thus, the hyperbaric partial pressures are retained in the aerosol particles even after the particles are exposed to ambient barometric pressure. The aerosolized particles can be inhaled to improve oxygenation and blood flow to the lung, or can be applied topically.

The devices may be configured to produce aerosol particles in a variety of different sizes. In some embodiments, the particles have mass median aerodynamic diameters of between about 0.25 and about 5 microns, thereby allowing sufficient deposition in the lung parenchyma, proximal to alveoli. Alternatively, the aerosolized particles can be topically applied to accelerate wound healing using larger sized aerosol particles such as 10.0 microns or greater.

The methods and devices maintain the liquid at a decreased temperature. In one embodiment, the temperature is below about 70° F. In another embodiment, the temperature is below about 55° F., preferably below about 45° F., and most preferably below about 40° F., prior to and during mixing with the gas. This temperature improves the solubility of the gas within the liquid and improves the hyperbaric partial pressures retained in the liquid solution. The temperature decrease of the gas and liquid allows gas partial pressures to remain dissolved in the liquid at levels greater than hyperbaric pressure, i.e., greater than 760 mm Hg.

A variety of different non-blood liquids may be used, including but not limited to saline, and other medications typically administered via the inhalation route such as bronchodilators, mucolytics, anti-inflammatory agents, antibiotics, surfactants, and combinations thereof.

The gas may include one or more different types of gases. The term "gas" is used herein to mean one or more of the various types of gases that may be placed into contact with the liquid. The different gas introduced to the liquid may include but are not limited to oxygen, carbon dioxide, helium, air, anesthetic gas, and combinations thereof.

Figure 1:
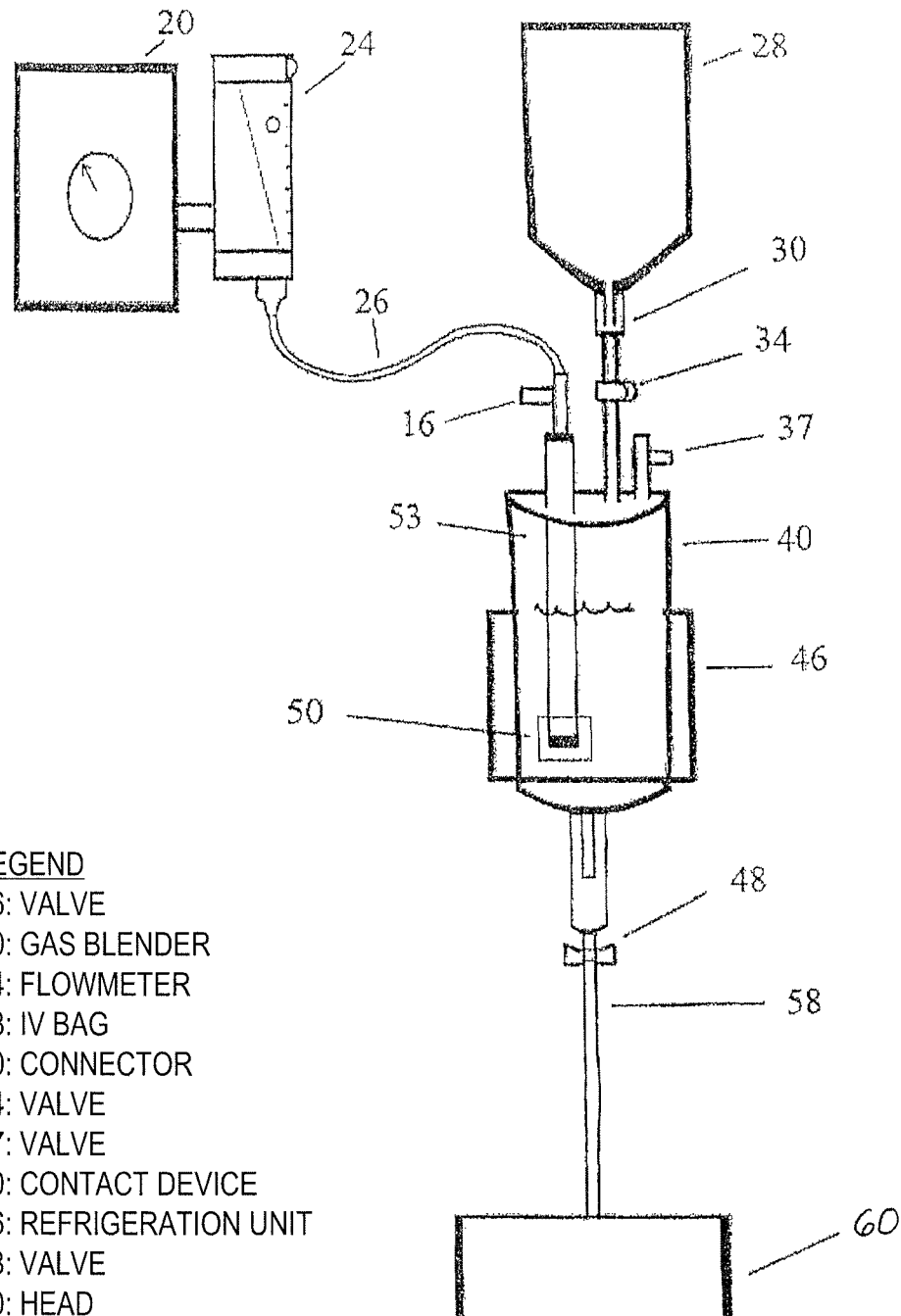
FIG. 1 is a schematic view of a system for dissolving a gas in a cooled liquid at ambient pressure.

FIG. 1 illustrates one embodiment for producing a liquid at ambient pressure with dissolved gas. It is understood that other embodiments may include the same or different elements depending upon the specific demands of the system. In this embodiment, the supersaturated liquid is created in the gas-liquid contact device 40 and then subsequently delivered to a device for aerosolization and delivery to the patient.

This system of FIG. 1 includes a sterile intravenous (IV) bag 28 with an outlet having a spike connector 30. A line extends from the connector 30 into a gas-liquid contact device 40. The gas-liquid contact device 40 may include a variety of different shapes and sizes. FIG. 1 includes the gas-liquid contact device 40 being a burette with a cylindrical shape with a volumetric graduation along its length with a roller clamp valve 48 at a lower end. A roller valve 34 is positioned along the line to control an amount of liquid that exits from the bag 28 such that a volume of liquid from the bag 28 may be infused into the gas-liquid contact device 40. FIG. 1 includes the supersaturated liquid being delivered to a container 60. Other embodiments may deliver the liquid through tubing to the device for aerosolization.

The system is further configured to introduce a gas into the gas-liquid contact device 40. This is accomplished through a gas blender 20 that is connected to a flowmeter 24. The flowmeter 24 in turn connects to a gas conducting tubing 26 that includes an inlet four-way stopcock valve 16. A tube 53 extends between the valve 16 and the gas-liquid contact device 40. The tube 53 is arranged so that gas from the gas conducting tubing 26 flows through the inlet four-way stopcock valve 16 and into a first end of the tube 53. The opposing second end of the tube 53 includes a bubble diffusing head 50 that is positioned beneath the surface of the liquid contained in the gas-liquid contact device 40. The gas-liquid contact device 40 connects to an adjustable stopcock valve outlet and filter 37. The adjustable stopcock valve outlet and filter 37 may operate as a vent in some embodiments.

A refrigeration unit 46 is positioned at the gas-liquid contact device 40 to cool the liquid. In one embodiment, the refrigeration unit 46 extends around a portion or entirety of an exterior of the gas-liquid contact device 40. Another embodiment includes the refrigeration unit 46 positioned at least partially within an interior of the gas-liquid contact device 40, but away from an interior space that contains the liquid. Still another embodiment includes the refrigeration unit 46 positioned within the interior space that contains the liquid. In one embodiment, the refrigeration unit 46 is configured to contain a refrigerant. A variety of different refrigerants may be used, including ice and water, cold pack gels, Freon, and others. The refrigeration unit 46 may also include thermal insulation that extends around a portion or entirety of the gas-liquid contact device 40 to assist in maintaining the liquid at the desired lower temperature.

As illustrated in FIG. 2, the system may also include a high pressure tank 120 connected through a regulator and tubing 110 to the inlet four-way stopcock valve 16. The tank 120 includes a different gas than is introduced through the gas blender 20 and flowmeter 24.

The gas introduced into the gas-liquid contact device 40 may include one or more different types of gases. In one embodiment using the system of FIG. 2, oxygen is introduced into the system through the blender 20/flowmeter 24 and a second gas is introduced from the tank 120. The different gas introduced through the tank 120 may include but are not limited to oxygen, carbon dioxide, helium, air, anesthetics gases, and combinations thereof. The term "gas" is used herein to mean one or more of the various types of gases that may be placed into contact with the liquid.

The gas selected for mixing may be based upon individual patient needs and may be rapidly mixed and administered using a variety of systems.

The process includes the liquid being slowly infused from the IV bag 28 into the gas-liquid contact device 40 to reach the desired level or volume of liquid. This may include insertion of the spike connector 30 into the outlet of the bag 28. The valve 34, which is closed prior to insertion of the spike 30, is subsequently opened to allow the liquid to fill the interior of the gas-liquid contact device 40 to the desired level. Following infusion of the liquid into the gas-liquid contact device 40, the gas is supplied to the gas blender 20 via high pressure gas conducting tubing (not illustrated). The desired gas concentration percentage and subsequent partial pressure to be dissolved in the liquid contained in the gas-liquid contact device 40 is selected on the gas blender 20. Once the desired gaseous partial pressure is selected on the gas blender 20, the gas travels from the gas blender 20 and flowmeter 24, through gas tubing 26 and 53, and into the gas-liquid contact device 40. Additional gas may be introduced in a like manner through the tank 120 and tubing 110 and 53. As the gas bubbles through the gas bubble diffusing head 50 at the end of the tubing 53, the gas mixes with the liquid contained in the gas-liquid contact device 40.

The temperature of the liquid in the gas-liquid contact device 40 at the time the gas is introduced may vary. In one embodiment, the liquid is previously cooled prior to the initial contact with the gas. The cooling may be done at a location other than the gas-liquid contact device 40 (e.g., the liquid is refrigerated prior to introduction into the device 40), or may be cooled in the device 40 by the refrigeration unit 46. In another embodiment, the liquid is at about room temperature when introduced into the device 40 and subsequently cooled at some point by the refrigeration unit 46.

At some point in time, the temperature of the liquid is decreased which increases the amount of dissolved gas in the liquid. In one embodiment, the temperature of the liquid is decreased to less than about 70° F. In another embodiment, the temperature of the liquid is decreased to less than about 55° F. In another embodiment, the temperature is decreased to less than about 45° F. Another embodiment includes decreasing the temperature to less than about 40° F.

In one embodiment that has gas supplied just through the blender 20, the flow rate of the gas is adjusted to about 3 L/min and allowed to bubble through the liquid for about 20 minutes. After contact with the liquid, the gas may be vented from the gas-liquid contact device 40 at the stopcock valve 37. The liquid is at ambient pressure during contact with the gas. The valve 37 may be adjusted to regulate the pressure within the gas-liquid contact device 40. In one embodiment, the initial position of the valve 37 is fully open to ambient air to allow venting of the inject gas. The valve 37 may remain fully open during the entire process. The valve 37 may also be adjusted to provide the desired internal pressure and allowing gas within the device 40 to be vented. In one embodiment, a manometer is coupled to the valve 37 to accurately regulate the internal pressure of the gas-liquid contact device 40.

The gas may be filtered to prevent contamination of the liquid both at entry into the gas-liquid contact device 40, and upon exiting the gas-liquid contact device at valve 37.

The liquid remains in contact with the gas in the gas-liquid contact device 40 until the liquid is supersaturated with the dissolved gas. In one embodiment, if oxygen is the desired gas to be mixed with the liquid, the oxygen and liquid are mixed within the gas-liquid contact device 40 until the partial pressure of the gaseous oxygen dissolved in the liquid is increased to greater than 760 mm Hg.

Figure 2:
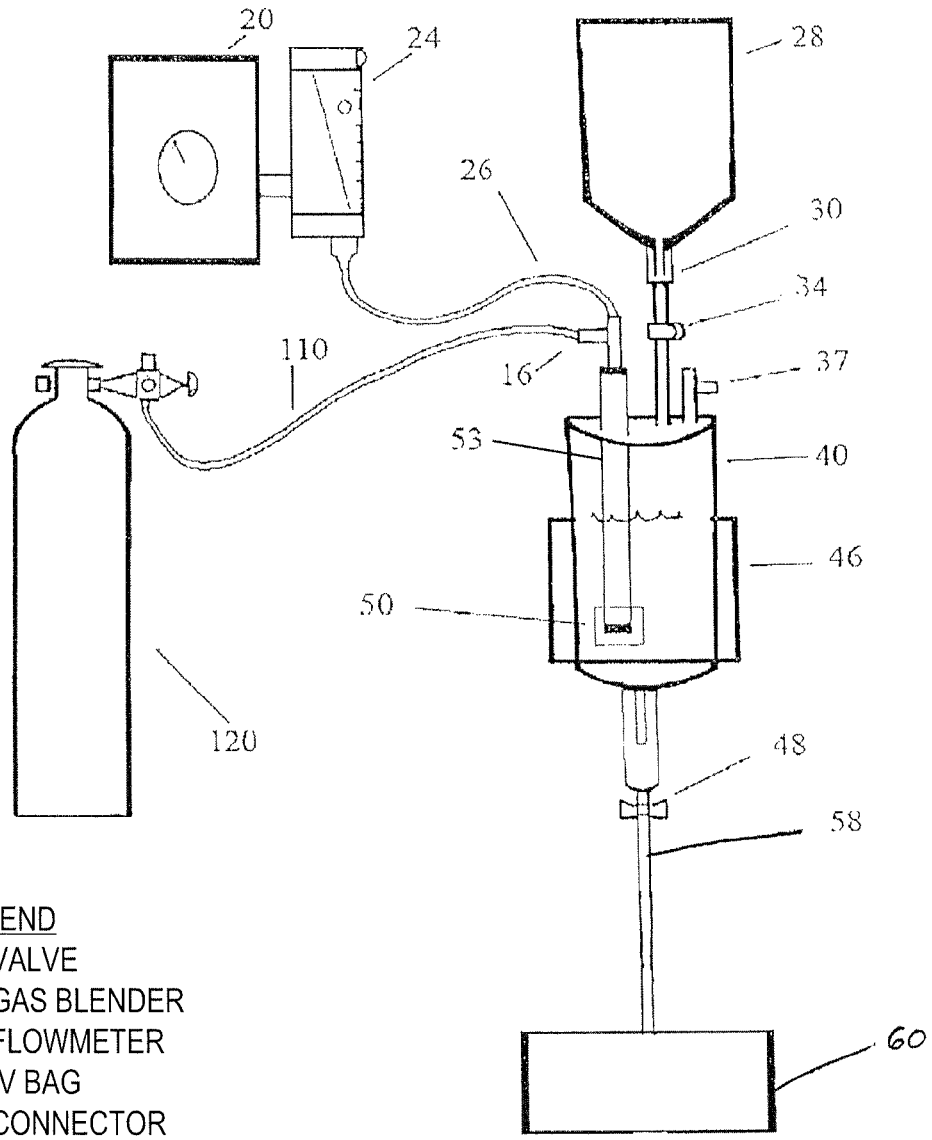
FIG. 2 is a schematic view of a system for dissolving gas in a cooled liquid at ambient pressure.

After bubbling the gas through the liquid, the liquid is maintained in the gas-liquid contact device 40 which prevents contamination with the external environment. The liquid is then delivered to a device for creating aerosol particles. In one embodiment as illustrated in FIG. 2, the liquid is delivered to a container 60, and then subsequently delivered to the device. Another embodiment includes the liquid being delivered through a tubing into the device.

Figure 3:
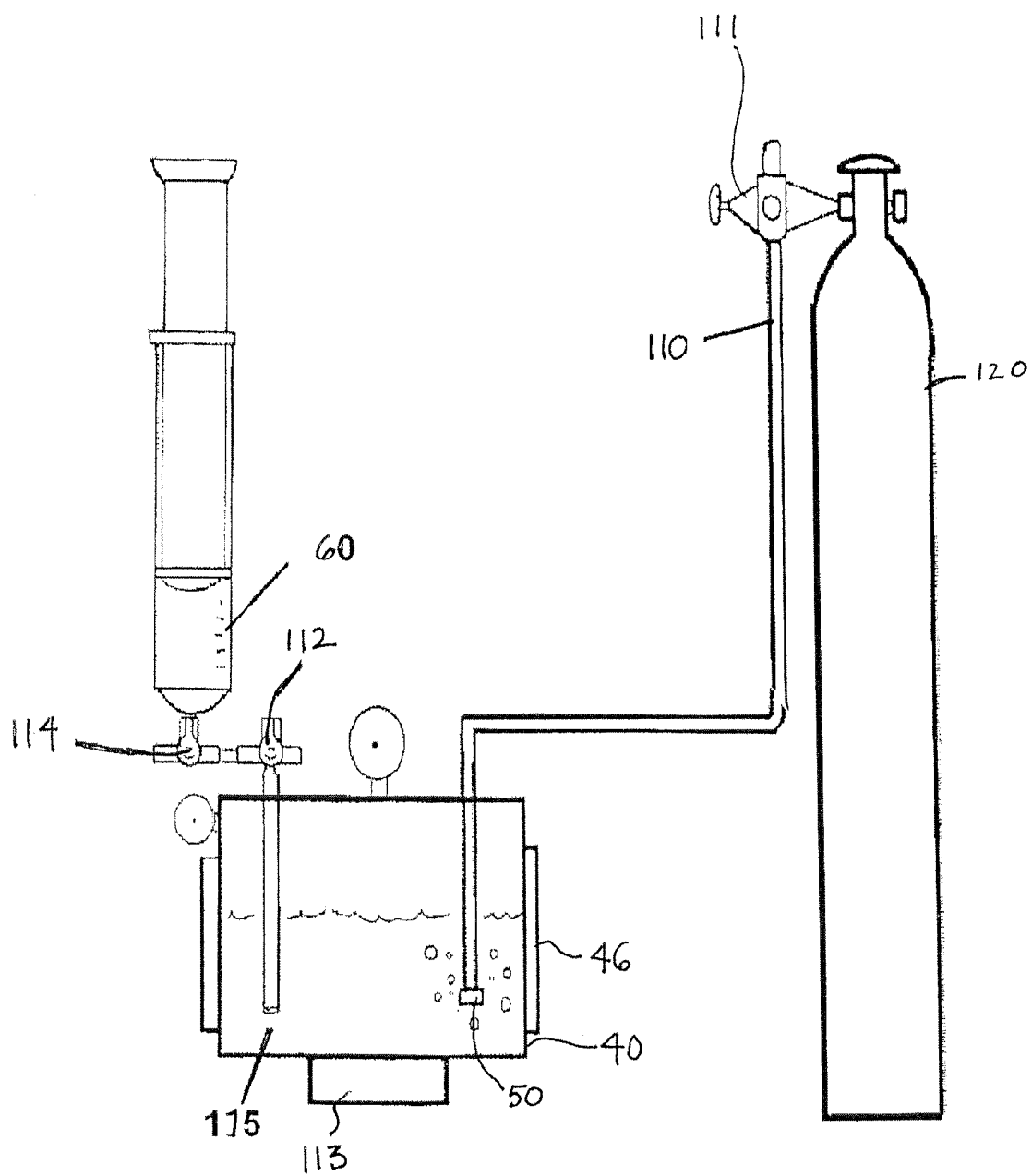
FIG. 3 is a schematic view of a system for dissolving gas in a cooled liquid at ambient pressure.

FIG. 3 illustrates another embodiment for supersaturating liquids with a gas. The liquid is initially stored in a container (not illustrated) that is connected to valve 112. The valve 112 is subsequently opened to allow the liquid to fill the device 40 to the desired level.

Following the infusion of the liquid, gas is delivered to the device 40 from a high pressure gas tank 120 having a gas pressure regulator with a flow regulating valve 111. An outlet of the valve 111 is connected to a tubing 110 that extends through an inlet and into the device 40. In one embodiment, the tubing 110 extends directly into the device 40, with another embodiment including the tubing 110 connected to a separate tubing at the inlet that extends into the device 40. The gas moves through the tubing 110 and is expelled through the diffusing head 50 positioned within the liquid. The liquid is at ambient pressure.

The device 40 receives a gas from the tank 120 by opening the valve 111 and allowing gas to flow through the tubing and into the device 40 through the diffusion head 50.

The gas is dissolved into the liquid through the contact as it is expelled through the diffusion head 50 and into contact with the liquid. The dissolving process may be further enhanced by an electromagnetic stirring device 113. In one embodiment, the stirring device 113 generates a magnetic field that improves mixing of the oxygen with liquids due to the paramagnetic properties of the oxygen molecules.

The liquid is maintained in the device 40 for a sufficient time so the partial pressure of the gaseous oxygen dissolved in the liquid is increased to at least 760 mm Hg.

After the liquid is supersaturated with gas, the liquid is withdrawn from the device 40. The liquid is either delivered directly to the device for aerosolization, or to one or more intermediate containers. In one embodiment as illustrated in FIG. 3, the liquid is moved to a container 60 that is a syringe that connects to a valve 114. The valve 112 is opened and valve 114 is subsequently opened to pull the liquid through a tube 115 and into the syringe.

The embodiments of FIGS. 1, 2, and 3 include the supersaturated liquid being produced at a location other than the aerosolization device, and then subsequently moving the supersaturated liquid to the device. The liquid remains at or near the lowered temperature to maintain the gas partial pressures at the selected values while being administered to the patient. The liquid may be delivered relatively quickly after exiting the gas-liquid contact device 40 thereby maintaining the lowered temperature.

Figure 4:
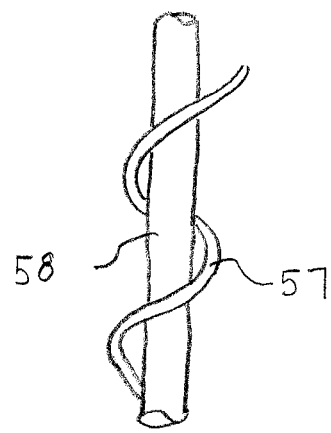
FIG. 4 is a side view of a cooling device wrapped around a tube carrying a liquid.
Figure 5:
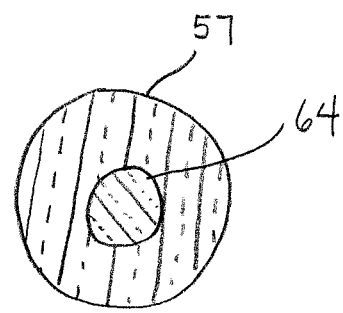
FIG. 5 is a sectional view of a tube carrying a liquid positioned within an interior of a cooling device.

In the various embodiments, the elements that receive the liquid (e.g., tubing 58, container 60) may be cooled to maintain the temperature of the liquid at the reduced temperature. In one embodiment, the tubing 58 is covered with a substance such as NEOPRENE®. In one embodiment as illustrated in FIG. 4, the tubing 58 is wrapped or braided with a tube 57 containing refrigerant. Another embodiment as illustrated in FIG. 5 includes the tubing 58 positioned inside a tube 57 containing a refrigerant. The container 60 may be cooled by packing it in an ice slush bath, applying a refrigerant to an exterior, or placing the container 60 in a refrigerator to maintain the temperature.

Figure 6:
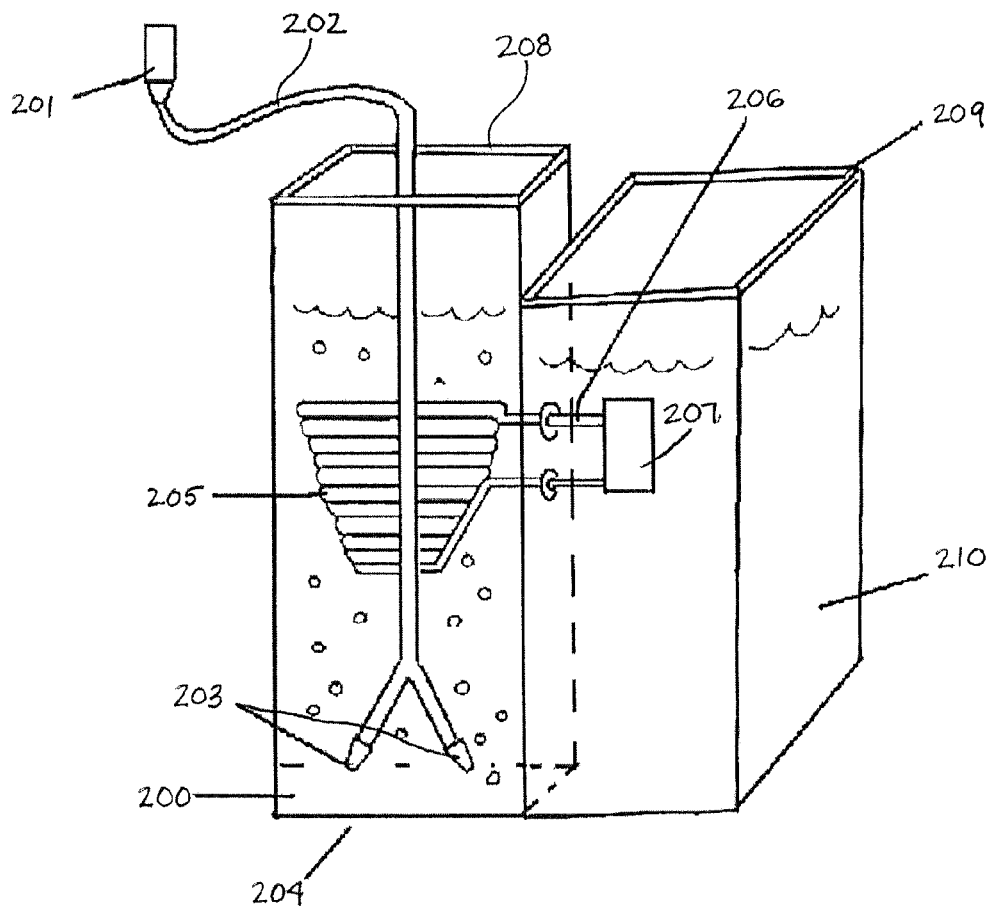
FIG. 6 is a schematic view of a system for dissolving a gas in a cooled liquid at ambient pressure.

FIG. 6 illustrates an embodiment of that includes a mixing gas-liquid contact device 200 that contains the liquid and a refrigerant chamber 210. Gas is introduced into the mixing gas-liquid contact device 200 through a gas flowmeter 201 and tubing 202. Tubing 202 extends into the mixing gas-liquid contact device 200 and is positioned with a distal end remaining beneath the surface of the liquid therein. In some embodiments, tubing 202 connects to at least one bubble diffusing head 203 that remains beneath the surface of the liquid. An outlet 204 is located on the bottom of the mixing gas-liquid contact device 200 to output the supersaturated liquid to a container. A refrigeration coil 205 is within the mixing gas-liquid contact device 200 and in contact with the liquid. The refrigeration coil 205 is connected to tubing 206 that extends between the mixing gas-liquid contact device 200 and the refrigerant chamber 210. A pump 207 connected to the tubing 206 is located in the refrigerant chamber 210. Both the mixing gas-liquid contact device 200 and the refrigerant chamber 210 may include removable covers 208, 209 respectively. The refrigerant chamber 210 may also include an outlet (not illustrated) at a lower section to remove the refrigerant.

In use, intravenous liquid is filled into the mixing gas-liquid contact device 200 and contained there at ambient pressure. The gas flowmeter 201 controls an amount of gas introduced into the system. Additional gas may be introduced through a separate tank in a similar manner to that illustrated in FIG. 2. The gas flows through the tubing 202 and the one or more bubble diffusing heads 203. As the gas exits through the bubble diffusing heads 203 and mixes with the liquid in the mixing gas-liquid contact device 200 until the liquid is supersaturated with the dissolved gas. Contact between the gas and the liquid is maintained until a supersaturated liquid having hyperbaric gaseous partial pressures is produced.

The temperature of the liquid in the mixing gas-liquid contact device 200 is lowered to increase the amount of dissolved gas. In one embodiment, the temperature is lowered to less than 70° F. In another embodiment, the temp-erature is lowered to less than 55° F. In another embodiment, the temperature is lowered to less than 45° F. In another embodiment, the temperature is lowered to less than 40° F. The temperature of the liquid may be lowered prior to delivery of the gas, during the delivery of the gas, after delivery of the gas, or combinations thereof.

To decrease the temperature, the separate refrigerant chamber 210 supplies refrigerant to the mixing gas-liquid contact device 200 via tubing 206. The tubing 206 is routed from the refrigerant chamber 210 into the interior of the mixing gas-liquid contact device 200 where it forms the refrigerant coil 205. The pump 207 in the refrigerant chamber 210 pumps the refrigerant through the tubing 206 and the refrigerant coil 205 in the mixing gas-liquid contact device 200. The refrigerant remains within the interior of the tubing 206 and the refrigerant coil 205 and does not directly contact the liquid contained within the mixing gas-liquid contact device 200. After the refrigerant flows through the coil 205, it is pumped through the tubing 206 and back to the refrigerant chamber 210 for re-cooling. Various types of refrigerant may be used, including but not limited to ice packs, gels, and Freon.

Once the desired amount of gas is dissolved into the liquid, the liquid is directed from the mixing gas-liquid contact device 200 through the outlet 204. The liquid is dispelled through the outlet 204 either to an intermediate container, or tubing that leads into an aerosolization device. Cooling methods as described above in FIGS. 4 and 5 may provide for keeping the liquid at a reduced temperature.

Spike Connector

The present application discloses the mixing of a gas with a cooled liquid at ambient pressure to form a supersaturated liquid that is later used in a nebulizer. This discovery now makes it possible to use existing equipment in combination with novel aspects disclosed in this application to form and deliver the liquid to the nebulizer. One embodiment provides for forming the liquid in a container such as an IV bag.

Figure 7:
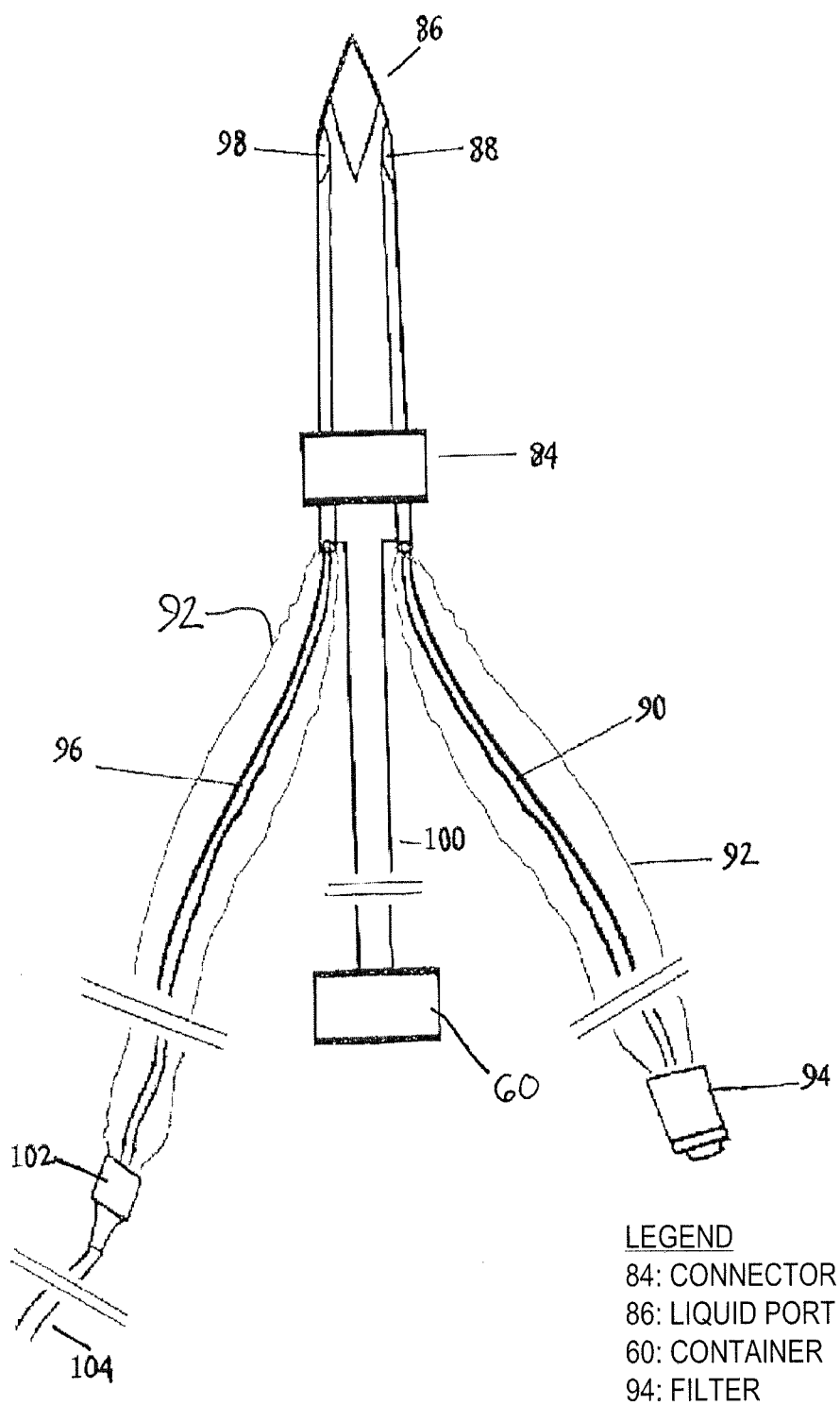
FIG. 7 is a side view of a connector for connecting with a liquid container.
Figure 8:
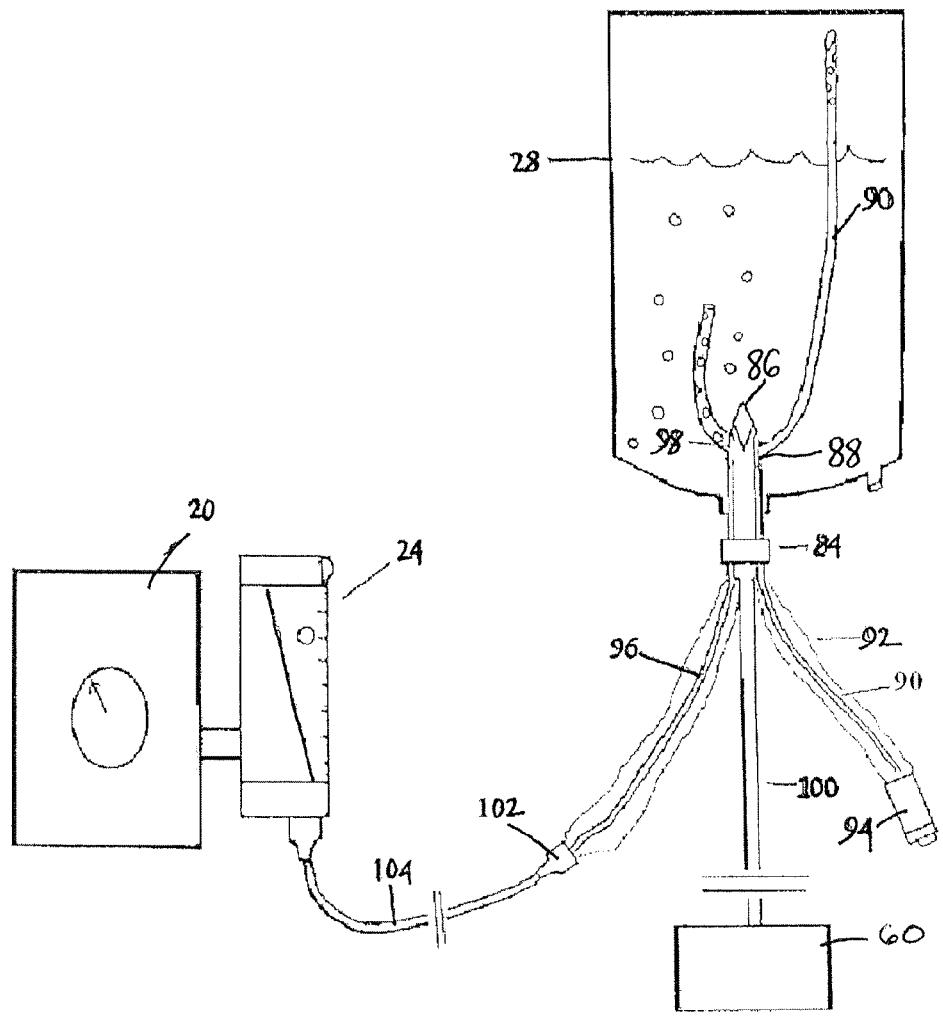
FIG. 8 is a schematic view of a connector inserted within a container for dissolving a gas in a cooled liquid at ambient pressure.

FIGS. 7 and 8 illustrate a spike connector 84 that is used with a liquid container, such as an IV bag 28 to practice the methods disclosed in the application. The connector 84 is configured to be inserted into an outlet of the IV bag 28 and provides for the mixing of the gas with the liquid directly within the bag 28 itself. As illustrated in FIG. 7, the connector 84 includes a leading end that is inserted into the container and an opposing trailing end that remains on the exterior of the container. The leading end may include a pointed tip to facilitate insertion into the bag. The connector 84 includes a liquid port 86 to remove the mixed liquid from the container 84. The connector 84 also includes a vent tube port 88 to accommodate a vent tube 90 and a gas insertion port 98 to accommodate a gas insertion tube 96. Each of the ports extends from generally the leading end to the trailing end of the connector 84.

The liquid port 86 provides for removing the mixed liquid from the container 28. Tubing 100 is connected to the port 86 and extends outward from the trailing end of the connector 84. The container 60 is positioned at the end of the tubing 100.

The vent tube 90 may be attached to the connector 84 at the time of insertion into the container, or may be attached after the insertion. The vent tube 90 is moved along the vent tube port 88 and into the container until the leading end is positioned above the liquid level. This positioning is illustrated in FIG. 8. A plastic sheath 92 may extend around the tube 90 where is extends outward from the connector 84 to prevent contamination of the tube 90. The plastic sheath 92 also maintains the container 28 as a closed, sterile system. The trailing end of the tube 90 is connected to a gas filter 94.

The gas insertion tube 96 may be attached to the connector 84 at the time of insertion into the container 28, or may be attached after the connector 84 is inserted into the container 28. The tube 96 is moved through the gas insertion port 98 with a leading end positioned below the level of the liquid towards a bottom of the container 28. In one embodiment, the leading end is positioned about ¼ of the distance from the bottom of the container 28. A plastic sheath 92 covers the tube 96 to maintain sterility of the liquid in the container 28. Further, a connector 102 may be positioned at the trailing end of the tube 96 to connect with the gas tubing 104.

The liquid in the container 28 may be cooled prior to insertion of the connector 84. In one embodiment, the container is stored in a refrigerator to chill the liquid to the necessary temperature, such as less than 55° F., less than 45° F., or less than 40° F. Cooling mechanisms, such as ice packs, may be attached to the exterior of the container 28 to keep the temperature of the liquid at the desired level and/or to cool the liquid to the desired temperature. In another embodiment, the temperature of the liquid is cooled after insertion of the connector 84.

In use, the connector 84 is inserted into the outlet of the container 28. The leading end is inserted through the outlet and into the interior of the container 28 with the trailing end remaining on the exterior of the container 28. The tube 96 is moved through the gas insertion port 98 to extend into the liquid. Further, the gas tubing 104 is attached to the connector 102. Likewise, the tube 90 is moved through the vent tube port with the leading end placed above the level of the liquid in the container 28.

The gas blender 20 is adjusted to the desired gas concentration and the flowmeter 24 is adjusted to the desired amount. In one embodiment, the flowmeter 24 is adjusted to a gas flow of about 3 L/min. The gas flows through the tubing 104, 96 and into the interior of the container 28 where it exits into contact with the liquid. In one embodiment, the gas bubbles through the liquid for about 20 minutes. Excess gas in the container 28 is vented through the tube 90 to the exterior. After the mixing is complete, the flowmeter 24 is turned off and the tube is clamped or otherwise placed in an off position.

The mixed liquid is removed from the container 28 through the liquid port 86, through tubing 100 and into a container 60 or through tubing and into the aerosolization device.

In the embodiments described above, the supersaturated liquid is delivered to a device where the liquid is changed into an aerosol for use with a patient. The supersaturated liquid may be continuously supplied to the device for continuous delivery of aerosol particles to the patient. The supersaturated liquid may also be intermittently supplied to the device for short duration treatments of aerosol particles to the patient. The short durations of aerosol application may vary in length, with examples including from about 3 minutes up to about 15 minutes. Examples of continuous flow nebulizers are disclosed in U.S. Pat. No. 5,277,175, herein incorporated by reference in its entirety.

Figure 9:
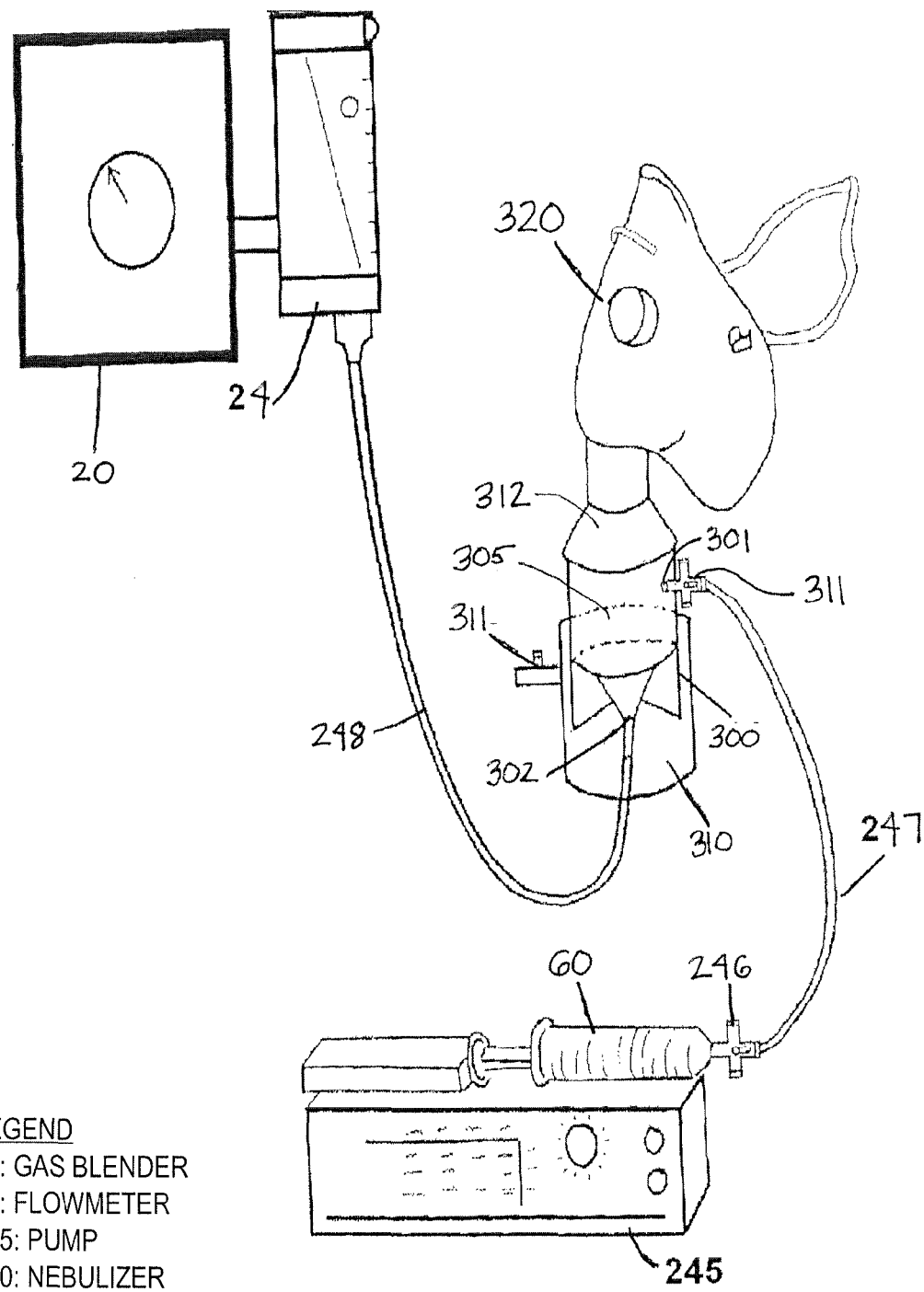
FIG. 9 is a system for creating aerosol particles including a nebulizer with a liquid input and a gas input.

FIG. 9 illustrates one embodiment of a device that receives the supersaturated liquid and creates aerosol particles and delivers them to the patient. The device includes a nebulizer 300 with a chamber 305 having a first inlet 301 for receiving the supersaturated liquid, and a second inlet 302 for receiving a gas that drives the nebulizer 300. The nebulizer 300 is configured to maintain the temperature of the supersaturated liquid and the aerosol particles at the lowered temperature. The nebulizer 300 includes a reservoir 310 that contains a refrigerant and extends around a portion or entirety of the chamber 305. The reservoir 310 may include a valve 311 to introduce the refrigerant to cool the chamber 305 and the liquid. In one embodiment, a liquid refrigerant such as ice water slush is input through the valve 311 and into the reservoir 310. Various other types of refrigerants may also be used, including but not limited to ice, ice slush, ice gel, chilled water, and chemical-made ice.

The supersaturated liquid is stored in a container 60 prior to being delivered to the nebulizer 300. In the embodiment of FIG. 9, the container 60 includes a syringe that is placed into an infusion pump 245 and connected to a stopcock valve 246. The valve 246 is connected to the inlet 301 of the nebulizer 300 through tubing 247.

The container 60 and/or tubing 247 may also be configured to maintain the liquid at the lowered temperature. In one embodiment, the tubing 247 is covered with a substance such as Neoprene R. In one embodiment as illustrated in FIG. 4, the tubing 247 is wrapped or braided with a tube containing refrigerant. Another embodiment as illustrated in FIG. 5 includes the tubing 247 positioned inside a tube containing a refrigerant. In the various cooling configurations, the refrigerant is not in direct contact with the liquid.

A gas is delivered to the nebulizer 300 through a separate tubing 248. The gas originates in a gas source connected to a gas blender 20 and adjusted with a flowmeter 24. The gas is delivered through the tubing 248 and into the second inlet 302 of the nebulizer 300 to power the nebulizer.

In use, the infusion pump 245 is adjusted for the flow of the liquid from the container 60 to match the aerosol output rate so that overfilling does not occur. Following injection of the liquid into the nebulizer 300, the gas flow rate is adjusted by the flowmeter 24. In one embodiment, a gas flowrate of about 4-7 L/min is used to power the nebulizer 300. The oxygen percentage driving the flowmeter 24 is adjusted by the gas blender 20.

The gas flow rate produces aerosol particles to be formed in the chamber 305. In one embodiment, the nebulizer 300 produces aerosol particles having mass median aerodynamic diameters of between about 0.25 microns and about 5.0 microns. This particle size allows sufficient deposition in the lung parenchyma, proximal to alveoli. The chamber 305 is maintained at the chilled temperature for the partial pressures of the dissolved gas to be maintained in the aerosol particles.

For treatment through aerosol inhalation, an aerosol mask 320 is connected to an outlet 312 of the chamber 305.

Alternatively, the method can be used to produce a supersaturated aerosol topically applied to wounds to stimulate healing and accelerate scar formation. For these applications, the mask 320 is removed from the nebulizer 300 and replaced with aerosol conducting tubing. The tubing is then placed proximally to the wound. Optionally, the therapeutic aerosol can be used in conjunction with ultrasonic generating transducers to act as a contact material to combine the therapeutic supersaturated liquid with ultrasonic treatment to accelerate wound healing. In the embodiments using an aerosol conducting tubing, the tubing may be cooled to maintain the high levels of dissolved gas in the aerosol. This may include wrapping the tubing with a refrigerant contained in a separate tubing similar to that disclosed in FIG. 4, or placing the tubing inside of a refrigerated tubing as illustrated in FIG. 5. In one embodiment with the supersaturated aerosol applied topically, the aerosol particles have mass median aerodynamic diameters of 10.0 microns or greater.

Figure 10:
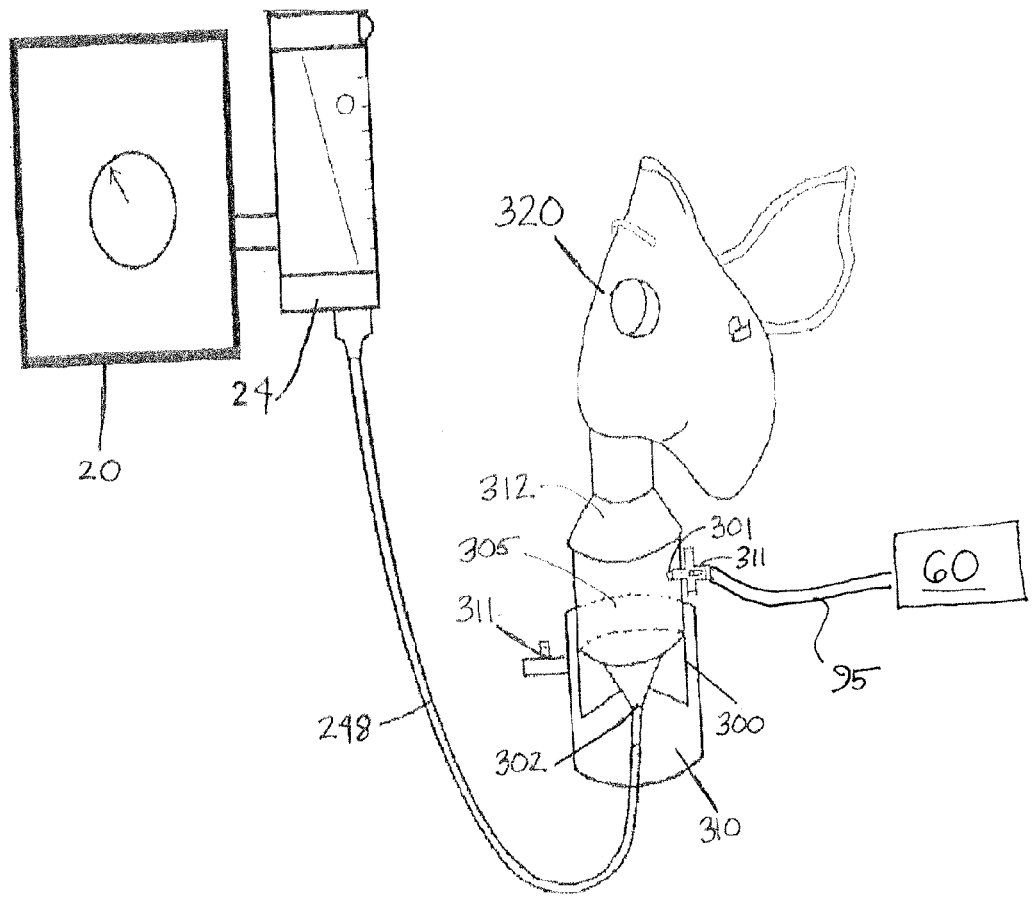
FIG. 10 is a system for creating aerosol particles including a nebulizer with a liquid input and a gas input.

FIG. 10 illustrates another embodiment in which the supersaturated liquid is delivered to the aerosolization device. In this embodiment, the liquid is input from the container 60 through a tubing 95 and into the chamber of the 300 through the first inlet 301. The input rate may be adjusted depending upon the desired outflow of the nebulizer 300. In this embodiment, the gas is delivered through the blender 20 and flowmeter 24 as described above for FIG. 9.

Figure 11:
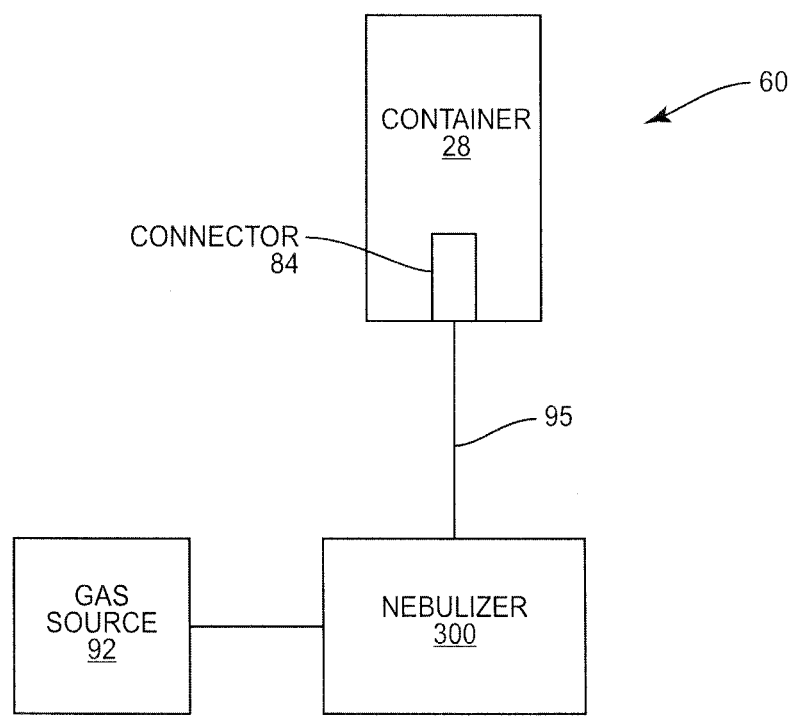
FIG. 11 is a schematic view of a system for creating aerosol particles.

FIG. 11 illustrates a similar embodiment with the container 60 including a bag 28 with a spike connector 84 as described above in FIG. 8. The supersaturated liquid is delivered from the container 60 through the tubing 95 and into the chamber of the nebulizer 300. The gas is delivered from the gas source 92 into the chamber of the nebulizer 300. In one embodiment, the gas source 92 may also be used for supplying gas to the liquid in the bag 28 through the spike connector 84.

In the embodiments described thus far, the supersaturated liquid is delivered to the device, such as a nebulizer 300. In other embodiments, the device also functions as a liquid-gas contact device to form the supersaturated liquid, in addition to creating an aerosol with the liquid for delivery to the patient.

Figure 12:
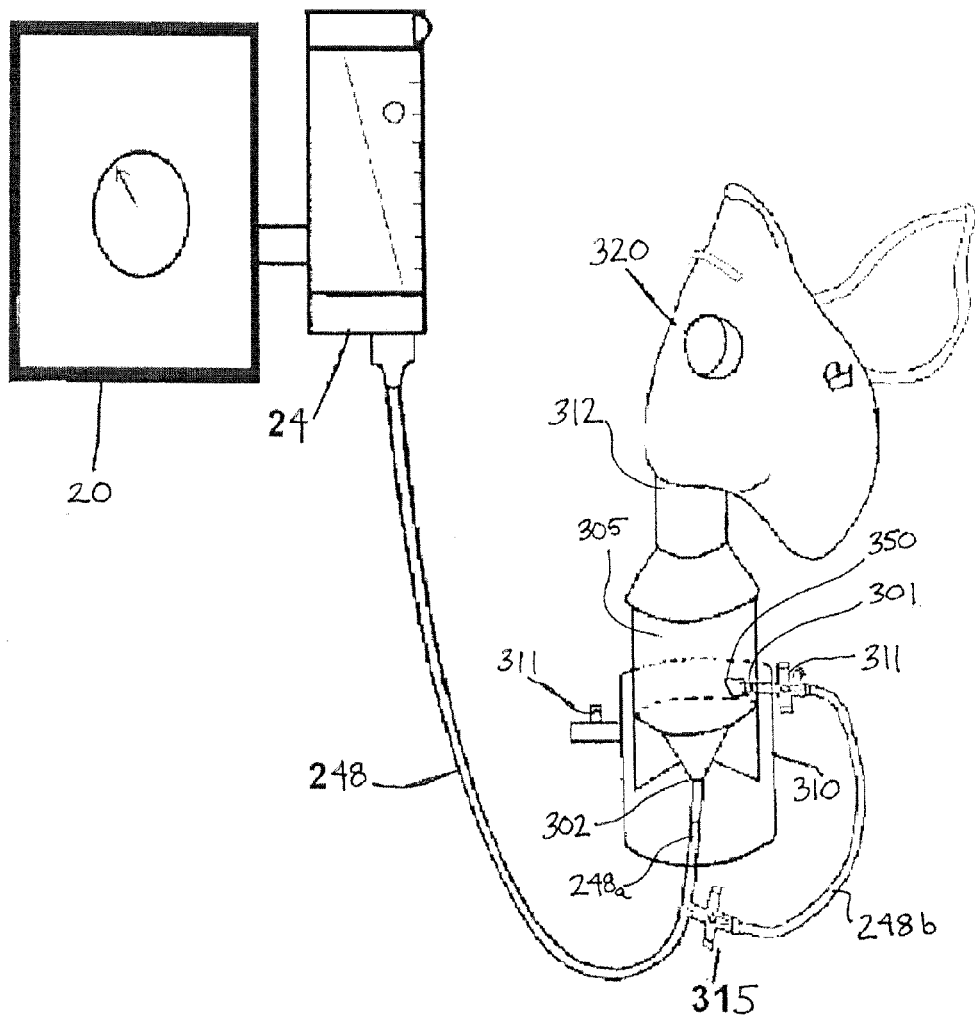
FIG. 12 is a system for creating aerosol particles within a nebulizer.

FIG. 12 illustrates one embodiment with the chamber 305 acting as the liquid-gas contact device. In use, the chamber 305 is initially filled with a liquid, such as saline or others described above. The liquid may be introduced into the chamber 305 through the inlet 301. In one embodiment, valve 311 includes an inlet that can be open to introduce the liquid or gas through the inlet 301 and into the chamber 305.

The nebulizer 300 may also include a reservoir 310 that contains a refrigerant and that extends around a portion or entirety of the chamber 305. The reservoir 310 may include a valve 311 to introduce the refrigerant to cool the chamber 305 and the liquid. The refrigerant may be used to cool the temperature of the liquid to below about 70° F. In one embodiment, the refrigerant cools the liquid to below about 55° F. In another embodiment, the liquid is chilled to below about 45° F. In one specific embodiment, the liquid is chilled to below about 40° F. As described above, the liquid may be chilled prior to and/or during and/or after the gas is introduced into contact.

The gas is delivered to the chamber 305 through the tubing 248. The tubing 248 includes a first branch 248a that leads to the second inlet 302 into the chamber 305. Tubing 248 also includes a second branch 248b that connects to the valve 311 at the first inlet 301. A valve 315 is positioned to adjust the flow of gas through the branch lines 248a, 248b. In addition, a diffusion head 350 is operatively connected to the first inlet 301. In one embodiment, tubing extends from the inlet 301 and into the lower reaches of the chamber 305 with the diffusion head 350 mounted at the end of the tubing.

In use, the liquid is initially placed into the chamber 305. The amount of liquid may vary depending upon the context of use. The liquid should extend over the diffusion head 350. The valve 315 is adjusted for the gas to flow through the second branch line 248b. In one embodiment, all the gas is directed through the second branch line 248b. In another embodiment, some of the gas still flows through the first branch line 248a and enters the chamber 305 through the second inlet 302. The gas through the second branch line 248b enters the chamber 305 through the first inlet 301 and diffusion head 350 into contact with the liquid.

The gas is bubbled through the liquid for a desired period of time similar to the embodiments described above. As in the previous embodiments, the chamber 305 is at ambient pressure during this process. Once the liquid becomes supersaturated with the introduced gas, the valve 315 is adjusted for the gas to move through the first branch line 248a and into the chamber 305. The gas flow rate may be adjusted by the flowmeter 24. In one embodiment, a gas flowrate of about 4-7 L/min is used to power the nebulizer 300. The oxygen percentage driving the flowmeter 24 is adjusted by the gas blender 20. The gas flow rate produces aerosol particles to be formed in the chamber 305. In one embodiment, the nebulizer 300 produces aerosol particles having mass median aerodynamic diameters of between about 0.25 microns and about 5.0 microns. The chamber 305 is maintained at lowered temperature for the dissolved gas to be maintained in the aerosol particles. For treatment through aerosol inhalation, an aerosol mask 320 is connected to an outlet 312 of the chamber 305.

Figure 13:
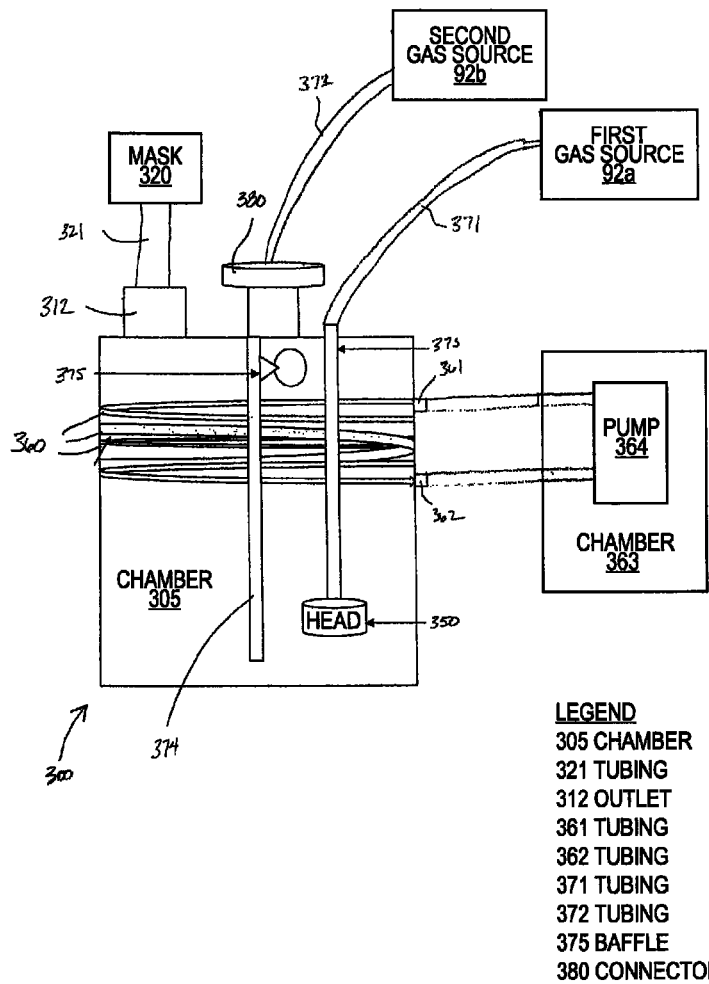
FIG. 13 is a schematic view of a system that includes a nebulizer chamber with a coil that extends from a refrigerant chamber.
Figure 14:
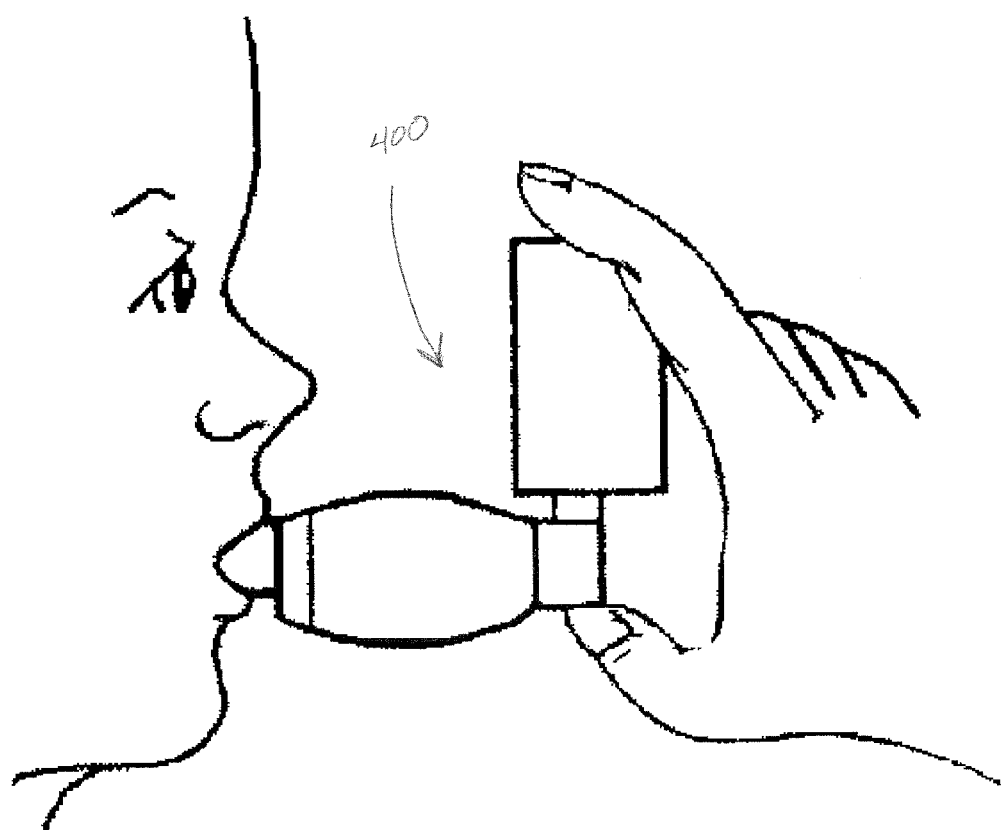
FIG. 14 is a side view of a metered dose inhaler.

FIG. 13 illustrates another embodiment where the chamber 305 acts as the liquid-gas contact device in addition to forming an aerosol. In this embodiment, the chamber 305 includes a refrigeration coil 360 that wraps around within the interior of the chamber 305. The coil 360 is connected to inlet tubing 361 and outlet tubing 362 that extends between the chamber 305 and a refrigerant chamber 363. A pump 364 connected to the tubing 361, 362 is located in the refrigerant chamber 363. Refrigerant from the chamber 363 enters the inlet tubing 361 and is pumped through the coil 360 to cool the liquid contained in the chamber 305. The refrigerant is then pumped through the outlet tubing 361 where it may exit back into the chamber 363. The refrigerant chamber 363 may also include an outlet (not illustrated) at a lower section to remove the refrigerant.

The refrigerant chamber 363 may be connected adjacent to the chamber 305, or may be spaced a distance away. In one embodiment, tubing 361, 362 each include extended lengths for the chamber 363 to be positioned away from the chamber 305.

The nebulizer 300 also includes first and second gas sources 92a, 92b. The gas sources may include various embodiments, including a blender 20 and flowmeter 24 as illustrated in FIG. 12, a blender 20 and flowmeter 24 with an additional gas tank input as illustrated in FIG. 2, and a gas tank input 120 as illustrated in FIG. 3.

The first gas source 92a includes a tubing 371 that is connected to a tubing 373 that extends toward a bottom of the chamber 305. A diffusion head 350 is positioned at the end of the tubing 373. The second gas source 92b also includes a tubing 372 that connects to a flow connector 380 for creating the aerosol particles. In one embodiment, the flow connector 380 includes a female nut that operatively connects with an end of the tubing 372. The flow connector 380 includes a tubing 374 that extends into the chamber 305, and a nebulizer jet and baffle 375.

In use, liquid is input into the chamber 305 to at least cover the diffusion head 350 and be in contact with the coil 360. The liquid is cooled within the chamber 305 by pumping the refrigerant from the refrigerant chamber 363 through the coil 360. Gas is also introduced into the chamber 305 from the first gas source 92a. In one embodiment, the gas flow rate is between about 4-7 L/min. The gas flows through the tubing 373 and is expelled through the diffusion head 350 and into contact with the liquid. The liquid may be cooled prior to and/or during and/or after contact with the gas. The liquid in the chamber 305 is at ambient pressure. The gas is placed into contact with the liquid until the liquid contains the desired amount of dissolved gas.

After this time, the second gas source 92b moves gas through the tubing 372 and into the flow connector 380. In one embodiment, the gas flow rate is greater than 10 L/min. The gas is moved through the tubing 374 following the Bernoulli Theorem and nebulizer jet and baffle 375 to create aerosol particles. The gas further forces the aerosol particles out of the chamber 305 through the outlet 312 to a mask 320. In one embodiment, tubing 321 extends between the outlet 312 and the mask 320 such that the mask 320 is distanced from the chamber 305. The pump 364 operates as the liquid is transformed into the aerosol particles. This maintains the high partial pressures of the dissolved gas in the aerosol particles.

In one embodiment, the nebulizer 300 of FIG. 13 with the internal coiling of the liquid has a higher capacity than the nebulizer 300 of FIG. 12 with the exterior cooling.

In the various embodiments of the nebulizers 300, medication, such as an artificial surfactant, can be injected into the chamber 305. The medication may be introduced through one of the various inlets into the chamber 305.

In some embodiments, the nebulizer 300 produces aerosol particles of a supersaturated liquid having hyperbaric gas partial pressures and thus is useful when it is desired to obtain aerosol particles of gaseous partial pressures between 760 mm Hg and 900 mm Hg.

Higher gas partial pressures may be desired for certain uses. In one embodiment, the device for delivering the aerosol includes a metered dose inhaler 400. This device delivers a specific amount of the aerosolized liquid in a short burst. The device includes a canister that houses the liquid, a metering valve that dispenses the liquid, and an actuator that operates the device and directs the aerosolized particles into the patient.

In the embodiments described above, the aerosol particles are delivered to the patient for inhalation. Another application is for delivering aerosol particles to the patient for topical application to accelerate wound healing. For use in topical application, the aerosol particles are normally larger than those for use with inhalation. In some embodiments, the aerosol particles have mass median aerodynamic diameters greater than about 10 microns.

The aerosol particles may be topically applied to the skin and body surfaces. When the particles contact the skin or body surface, the oxygen may be directly absorbed into the tissue and body fluids by means of diffusion. This type of application may be especially useful in the treatment of wounds which have a poor blood supply. It has been found that adequate tissue oxygenation is necessary for normal healing to occur. Frequently, the local circulation of blood is disrupted when a wound occurs, thereby limiting the available oxygen delivered by the blood to injured tissue. Wounds deprived of oxygen heal very slowly or not at all. Oxygen is essential to healing in 3 ways: (1) the formation of granulation (scar) tissue consumes oxygen, (2) molecular oxygen is essential for the hydroxlyation of proline and lysine during collagen synthesis by fibroblast cells, and (3) an optimal tissue $pO_2$ must be maintained for cellular proliferation of fibroblast cells which are essential for collagen synthesis and healing to occur. In essence, the topical application of aerosol particles allows adequate tissue oxygenation even when blood flow is disrupted. When adequate tissue oxygenation is maintained, both the rate and tensile strength of wound healing are increased.

Figure 15:
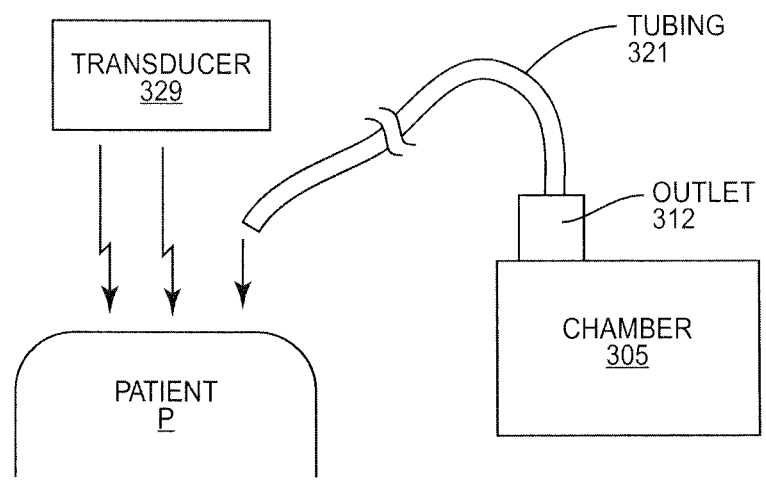
FIG. 15 is a schematic view of a chamber with an outlet and tubing for topical application of aerosol particles.

FIG. 15 illustrates an embodiment for topical application of aerosol particles. A chamber 305 holds the aerosol particles which are directed to an outlet 312 as described in the various embodiments above. The aerosol particles are than delivered through tubing 321 for application to the patient. The length, structure, and configuration of the tubing 321 may vary depending upon the context of use.

In some embodiments, the treatment of the patient P includes just the topical application of the aerosol particles. Other embodiments include the application of aerosol particles in combination with ultrasound. FIG. 15 includes an ultrasound transducer 329 positioned in proximity to the patient P for applying sound waves to the desired area on the patient P. The frequency of the sound waves may vary, with one range being between out 0.7 to about 3.3 MHz.

The topical application of aerosol particles accelerates wound healing in a variety of different contexts, including but not limited to treatment of pressure sores on the skin, skin ulcers, burns, and wounds following surgery.

The use of oxygen therapy including topical application is disclosed in U.S. Pat. No. 5,084,011, hereby incorporated by reference in its entirety.

In the various embodiments, a variety of different gases may be used. Note that a gas other than oxygen may be used, such as helium oxide mixtures. In one embodiment, the method described herein can be used to produce an aerosol of dissolved-helium and oxygen in a liquid such as saline or sterile water. When inhaled, an aerosol of this composition may alter pulmonary blood flow and decrease pulmonary vascular resistance.

In other embodiments, the above described methods can be used to generate negatively charged electro aerosols having hyperbaric levels of dissolved gases. Such electro aerosols are created by supersaturating liquid with gas containing an inherently negative charge within the molecule itself, such as molecular oxygen. Electro aerosols can be used for antimicrobial purposes, improved airway clearance, bronchodilator, and neutralization of positively charged particles within the lung, such as Charcot Leydan crystals. These crystals are released from eosinophil cells which may cause intense bronchospasm in asthma. The effects of negatively charged electro aerosols correlate with the partial pressure of oxygen dissolved in the aerosolized liquid.

During experimental testing, it was shown that dissolved oxygen tension in the supersaturated liquid remained greater than the barometric pressure following aerosolization of the liquid. Such finding was unexpected. Rather, it was expected that when small particles having a high surface area are exposed to air, the oxygen would diffuse out of the particles. These findings are illustrated in FIG. 16.

The aerosolizing devices described herein regulate the pressures of the liquid to be aerosolized so to maintain hyperbaric dissolved gas partial pressures within the liquid. The devices maintain a cold temperature that allows the liquid to keep supersaturated through the process to create an aerosol. The gas partial pressures are maintained while in the device environment. The gas solubility and resulting partial pressure is inversely related to the temperature of the liquid, and more gas may be dissolved at higher partial pressures when the liquid temperature decreases.

The aerosolizing devices may produce aerosol particles having mass median aerodynamic diameters of between approximately 0.25 and approximately 5 microns, thereby allowing sufficient deposition in the lung parenchyma, proximal to alveoli. In one embodiment, the temperature of the liquid is maintained at a decreased temperature, preferably approximately 44° F., prior to and during mixing with the gas, to improve the solubility of the gas within the liquid and improve the hyperbaric partial pressures retained in the liquid solution. The temperature decrease of the gas and liquid allows gas partial pressures to remain dissolved in liquid at levels greater than hyperbaric pressure, i.e., greater than 760 mm Hg.

In the various methods, the contact between the liquid and gas is controlled to dissolve the desired amount of gas into the liquid. The amount of dissolved gas can be controlled by one or more parameters, such as but not limited to: type of liquid, type of gas, temperature of the liquid, the gas flow rate, amount of time the gas is in contact with the liquid. Controlling the desired partial pressure of oxygen in the liquid allows the partial pressure of the gas to be titrated according to an individual patient's needs. This may avoid exposure to excessive gas concentrations. In one embodiment, the gas dissolved in the liquid is selected to infuse the liquid with a precise dissolved gas partial pressure and achieve normal blood oxygen levels for a patient.

Co-pending U.S. patent application Ser. No. 13/410,164 entitled Devices and Methods for Making and Administering an Intravenous Liquid with Supersaturated Dissolved Gas and filed on the same day as the present application discloses devices and methods for making a supersaturated liquid and administering the liquid to a patient, and is hereby incorporated by reference in its entirety.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of aerosol therapy comprising:
   forming in a non-pressurized vessel a non-blood liquid supersaturated with oxygen gas, the liquid being at a temperature below about 55° F. and at ambient atmospheric pressure;
   transforming the liquid into aerosol particles that remain supersaturated with the oxygen gas, the aerosol particles remaining at a temperature below about 55° F.; and
   delivering the aerosol particles to the patient while the aerosol particles remain supersaturated with the oxygen gas.

2. The method of claim 1, further comprising supersaturating the liquid with the oxygen gas and transforming the liquid into the aerosol particles in a chamber.

3. The method of claim 2, further comprising continuously delivering the supersaturated liquid into the chamber while transforming the liquid into the aerosol particles.

4. The method of claim 1, wherein the supersaturated liquid is formed in a first chamber and transferred to a second chamber, and the aerosol particles are formed in the second chamber.

5. The method of claim 1, further comprising transforming the liquid into the aerosol particles that include mass median aerodynamic diameters greater than 10 microns for topical application.

6. The method of claim 5, further comprising applying ultrasound waves to the patient in combination with the aerosol particles.

7. A method of aerosol therapy comprising:
   mixing a gas with a non-blood liquid while the liquid is at a decreased temperature of below about 55° F. and at ambient atmospheric pressure, the mixing occurring in a non-pressurized vessel;
   maintaining the liquid in contact with the gas at ambient atmospheric pressure and below about 55° F. until the partial pressure of the gas in the liquid is greater than 760 mm Hg;
   transforming the liquid into aerosol particles with the partial pressure of the gas in the aerosol particles remaining at greater than 760 mm Hg; and
   delivering the aerosol particles to the patient.

8. The method of claim 7, wherein the liquid is at a temperature of less than 55° F. during the mixing with the gas and while being transformed into the aerosol particles.

9. The method of claim 7, further comprising decreasing the temperature of the liquid to less than 55° F. after the gas is in contact with the liquid.

10. The method of claim 7, further comprising mixing the gas with the liquid until the partial pressure of the gas in the liquid is greater than 760 mm Hg in a first device, transferring the liquid to a second device, and transforming the liquid into the aerosol particles in the second device.

11. The method of claim 10, further comprising continuously transferring the liquid to the second device while transforming the liquid into the aerosol particles.

12. The method of claim 11, further comprising dripping the liquid into the second device.

13. The method of claim 10, further comprising moving a refrigerant through a coil in the first device and cooling the liquid.

14. The method of claim 7, further comprising transforming the liquid into the aerosol particles that include mass median aerodynamic diameters of between about 0.25 microns and about 5.0 microns for deposition in the lung parenchyma proximal to alveoli when the aerosol particles are delivered to the patient.

15. The method of claim 7, further comprising transforming the liquid into the aerosol particles that include mass median aerodynamic diameters greater than 10 microns for topical application and applying ultrasound waves to the patient in combination with the aerosol particles.

16. A method for aerosol therapy comprising:
   containing a non-blood liquid at ambient atmospheric pressure in a gas-liquid contact device in a nebulizer, the gas-liquid contact device being non-pressurized;
   introducing a gas into the gas-liquid contact device and bubbling the gas through the liquid, the liquid being at a temperature of below about 70° F.;
   maintaining the liquid in contact with the gas at the ambient atmospheric pressure and the liquid at below about 70° F. until a partial pressure of the gas in the liquid is at least 760 mm Hg;
   transforming the liquid into aerosol particles within the gas-liquid contact device while maintaining the aerosol particles at below about 70° F. and the partial pressure of the gas at greater than 760 mm Hg; and
   delivering the aerosol particles through an outlet in the gas-liquid contact device to the patient.

17. The method of claim 16, further comprising moving a refrigerant into a reservoir on an exterior of the gas-liquid contact device and cooling the liquid and the aerosol particles in the gas-liquid contact device.

18. The method of claim 16, further comprising moving a refrigerant through a coil in the gas-liquid contact device and cooling the liquid while the gas is bubbling through the liquid.

19. The method of claim 16, further comprising moving a refrigerant through a coil in the gas-liquid contact device and cooling the aerosol particles.

20. The method of claim 16, further comprising introducing a second gas into the gas-liquid contact device to form the aerosol particles and to move the aerosol particles through the outlet and to the patient.

21. The method of claim 16, further comprising transforming the liquid into the aerosol particles that include mass median aerodynamic diameters of between about 0.25 microns and about 5.0 microns for deposition in the lung parenchyma proximal to alveoli when the aerosol particles are delivered to the patient.

22. The method of claim 16, further comprising transforming the liquid into the aerosol particles that include mass median aerodynamic diameters greater than 10 microns for topical application to the patient.

* * * * *